United States Patent [19]
Takagi et al.

[11] Patent Number: 4,783,159
[45] Date of Patent: Nov. 8, 1988

[54] OPERATION MICROSCOPE

[75] Inventors: Kazutoshi Takagi; Nobuaki Kitajima, both of Tokyo, Japan

[73] Assignee: Tokyo Kogaku Kikai Kabushiki Kaisha, Japan

[21] Appl. No.: 31,523

[22] Filed: Mar. 26, 1987

[30] Foreign Application Priority Data

Mar. 31, 1986 [JP] Japan .............................. 61-47963[U]

[51] Int. Cl.⁴ ...................... G02B 21/06; G02B 21/12; G02B 21/22
[52] U.S. Cl. .................................... 350/516; 350/526; 350/527; 350/528
[58] Field of Search .............. 350/523, 526, 527, 528, 350/507, 511, 515, 516

[56] References Cited

U.S. PATENT DOCUMENTS

| | | | |
|---|---|---|---|
| 4,232,933 | 11/1980 | Nakahashi | 350/523 |
| 4,329,015 | 5/1982 | Feinbloom | 350/516 |
| 4,361,379 | 11/1982 | Klein . | |
| 4,428,035 | 1/1984 | Müller et al. . | |
| 4,479,700 | 10/1984 | Abe | 350/523 |
| 4,614,411 | 9/1986 | Horenz | 350/516 |
| 4,657,357 | 4/1987 | Nishimura et al. | 350/516 |

Primary Examiner—Jon W. Henry
Attorney, Agent, or Firm—Brumbaugh, Graves, Donohue & Raymond

[57] ABSTRACT

An operation microscope in which the optical axis of the illumination optical system is in alignment with the optical axis of the objective lens of the observation optical system and the illumination rays pass along the optical axis of the objective lens. Due to this construction, it is possible to sufficiently illuminate the deep parts of diseased tissue in, for example, a cataract operation, and very easy to confirm whether or not any part of the lens remains in the capsula lentis after the removal of the lens of the eye.

5 Claims, 4 Drawing Sheets

OPERATION MICROSCOPE

BACKGROUND OF THE INVENTION

This invention relates to an operation microscope for use in ophthalmic and surgical operations and more particularly to a microscope for use in surgical operations in which two observation rays entering respectively to the left and right eyes of an operator and illumination rays pass through a single objective lens.

Especially in microscopes for use in surgical operations in ophthalmology and otorhinology it is preferable to so construct the microscope that the illumination rays and the observation rays cross each other at the smallest possible angle in order to illuminate deep parts of the diseased tissue. For example, using a microscope to confirm whether or not a part of the lens of an eye remains in the capsula lentis after the removal of the lens in a cataract operation, it is impossible to reliably confirm the presence or absence of any remaining part of the lens by illuminating the lens and the capsula lentis from the front side thereof, since both the lens and the capsula lentis are transparent. Accordingly, it has been the usual practice to confirming whether any part of the lens remains by illuminating the fundus through the capsula lentis so that rays reflected by the fundus pass through the capsula lentis from the back side thereof.

In such confirming work, it is impossible to sufficiently illuminate the fundus because of interruption by the pupil if the optical axis of the observation optical system and the optical axis of the illumination optical system cross each other at a large angle, and therefore it is very difficult to reliably confirm whether any part of the lens remains in the capsula lentis.

Taking the circumstances mentioned above into consideration, there has heretofore been proposed a microscope for use in surgical operation wherein the illumination rays enter a single objective lens in parallel with the optical axis of the single objective lens at a point perpendicularly offset from the center point of a line connecting the points of incidence of two observation beams, whereby the illumination rays are refracted by the single objective lens are directed to the focal point of the single objective lens.

However, this prior art microscope in which the illumination rays enter the single objective lens at the periphery thereof, has a problem in that it is impossible to sufficiently illuminate deep parts of the diseased tissue because of misalignment of the optical axes of the observation rays and the illumination rays.

SUMMARY OF THE INVENTION

It is an object of the present invention to provide a operation microscope which has aligned observation and illumination ray optical axes and is able to sufficiently illuminate the deep parts of the diseased tissue.

According to the present invention, the above and other objects can be accomplished by an operation microscope having a pair of observation optical systems behind a single objective lens characterized in that the microscope is provided with an illumination apparatus behind said single objective lens, said illumination apparatus having an exit optical axis in alignment with an optical axis of said single objective lens and a reflecting member for reflecting illumination rays.

In a preferable aspect of the present invention, said reflecting member is disposed in a space between said single objective lens and said observation optical systems. According to a specific aspect of the present invention, said refecting member is so mounted that it can be selectively moved in and out of the optical axis of the objective lens. In another aspect of the present invention, said illumination apparatus comprises illumination means for generating illumination rays at a position outside said optical axis of the single objective lens, and optical transmitting means for directing one part of the illumination rays to said reflecting member. In a further preferable aspect of the present invention, said optical transmitting means is a reflecting member for reflecting the illumination rays toward said reflecting member.

BRIEF DESCRIPTION OF THE DRAWINGS

Embodiments of the present invention are illustrated in the drawings wherein.

DESCRIPTION OF THE PREFERRED EMBODIMENTS

Figure 1:
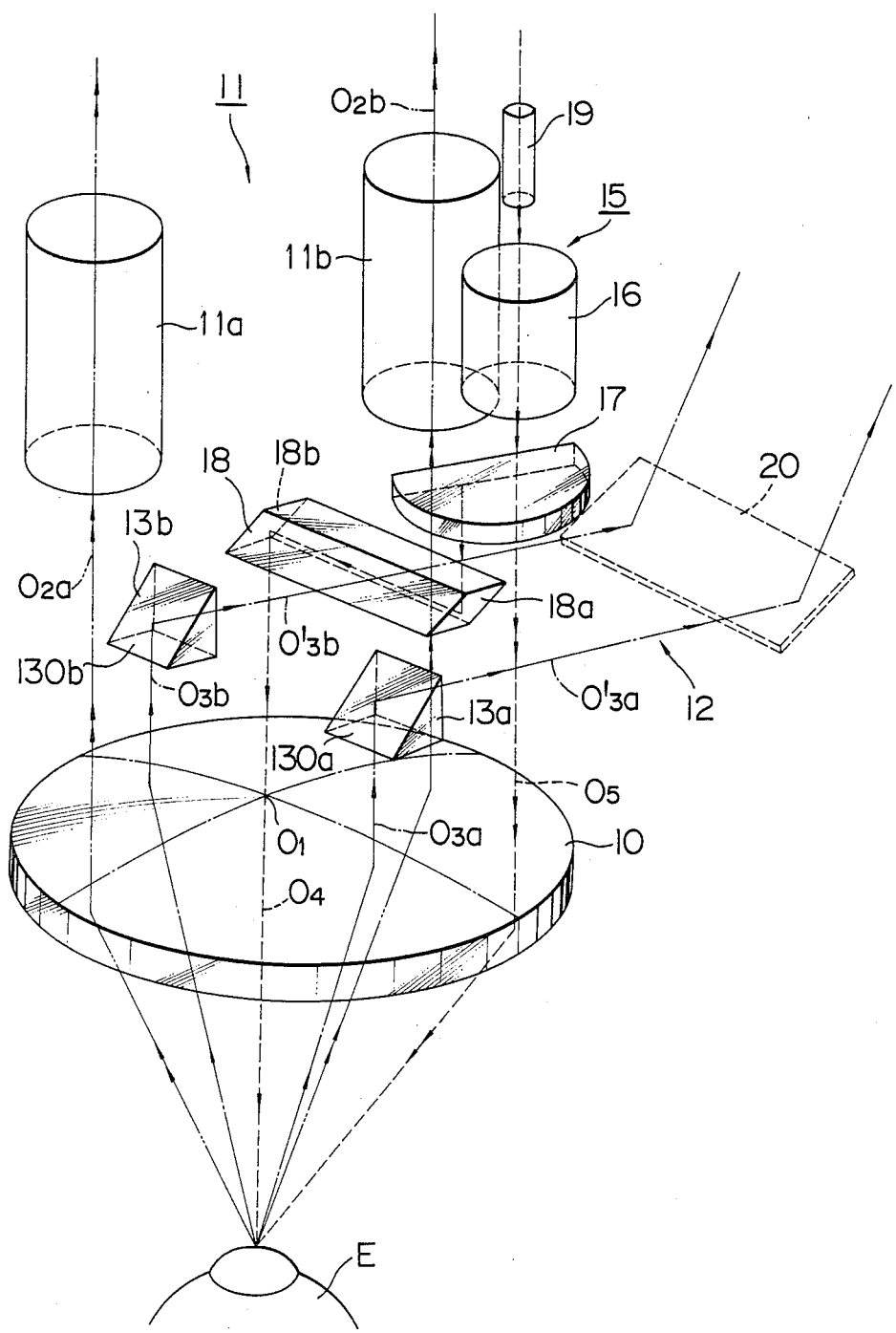
FIG. 1 is a perspective view showing the structural arrangement of the main optical parts of the operation microscope of the present invention.

FIG. 1 is a perspective view of the optical arrangement of the microscope for surgical operation of the present invention. A first observation optical system 11 to be used by the operator is positioned above a single objective lens 10 used by both the left and right eyes of the operator. The first observation optical system 11 comprises a variable power zoom optical system 11a for the left eye, a variable power zoom optical system 11b for the right eye, erecting optical systems respectively for the left and right eyes, and eyepieces (not shown).

Reflecting prisms 13a and 13b are disposed between the objective lens 10 and the first observation optical system 11 for the operator. A plane including incident optical axes $O_{3a}$ and $O_{3b}$ entering the reflecting prisms 13a and 13b and a plane including optical axes $O_{2a}$ and $O_{2b}$ of the first observation optical system 11 cross each other at a position through which an optical axis $O_1$ of the objective lens 10 passes.

The incident optical axes $O_{3a}$ $O_{3b}$ entering the reflecting prisms 13a and 13b are refracted respectively by reflecting surfaces 130a and 130b of the reflecting prisms and exit optical axes $O'_{3a}$ and $O'_{3b}$ exiting from the reflecting prisms 13a and 13b are included in a plane perpendicular to the optical axis $O_1$ of the objective lens 10. These exit optical axes $O'_{3a}$ and $O'_{3b}$ are reflected by a reflecting mirror 20 and emitted as incident optical axes to a known assistant microscope which use a common objective lens with the objective lens of the operation microscope.

An illumination optical system 15 is disposal at one side of the first observation optical system 11. The illumination optical system 15 comprises an optical fiber 19 for guiding rays from a light source (not shown), a variable power zoom optical system 16 for varying the illumination field, and a projection lens 17. The illumination rays passing through the projecting lens 17 pass through the objective lens 10 and illuminate a diseased tissue such as an eye E to be operated on.

One part of the illumination rays from the projecting lens 17 enter a reflecting prism 18 and illuminate the eye E to be operated on through the objective lens 10 after having been reflected by two reflecting surfaces 18a and 18b of the prism 18. In this case, an exit optical axis $O_4$ from the reflecting prism 18 is in alignment with the optical axis $O_1$ of the objective lens 10 and passes through the optical axis $O_1$. Accordingly, the illumination rays from the reflecting prism 18 pass along the optical axis $O_1$ of the objective lens 10 and make it possible to illuminate deep parts of the eye E to be operated on.

Figure 2:
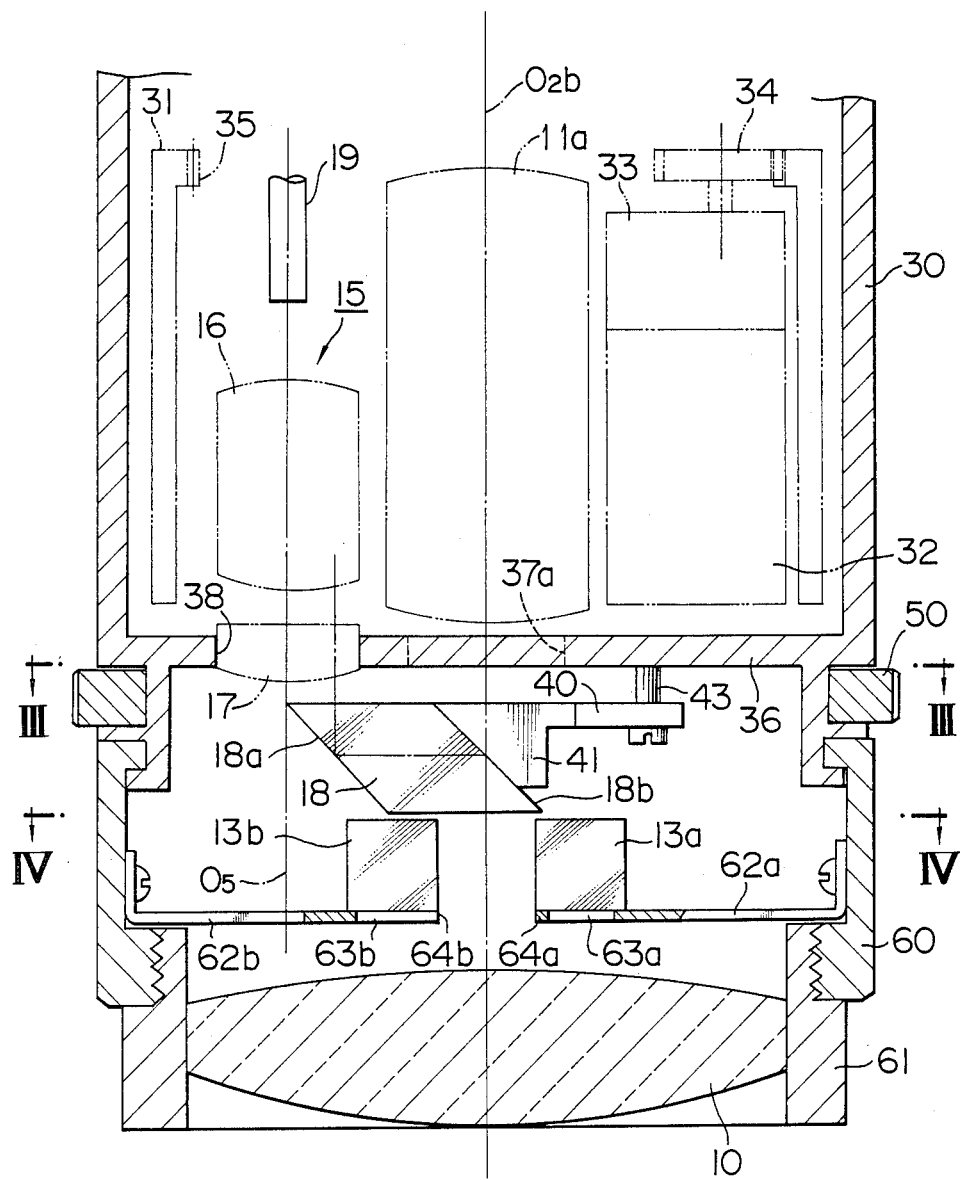
FIG. 2 is a longitudinal cross-sectional view of the microscope of the present invention.
Figure 3:
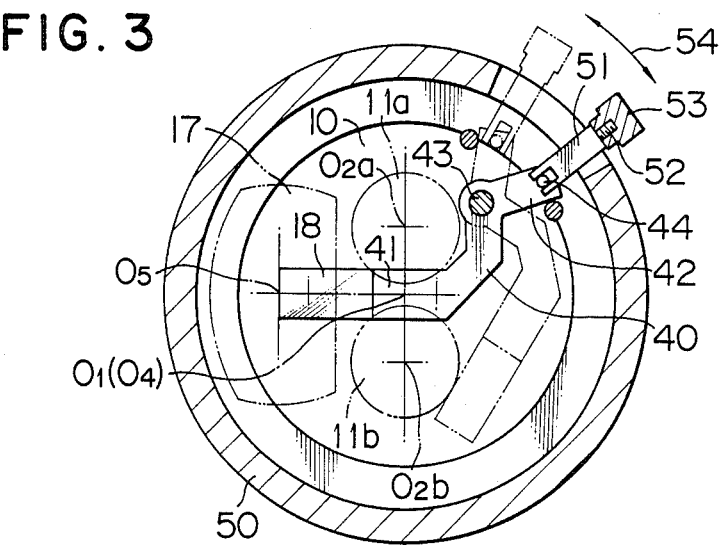
FIG. 3 is a cross-sectional view taken along lines III—III of FIG. 2.
Figure 4:
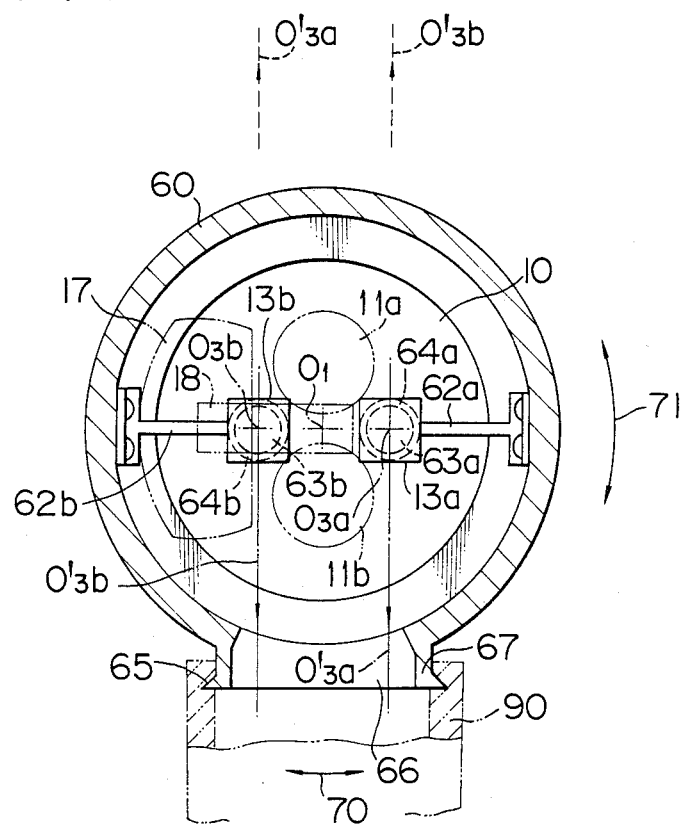
FIG. 4 is a cross-sectional view taken along lines IV—IV of FIG. 2.

FIGS. 2 through 4 shows the mechanical structure of the microscope embodying the above mentioned optical system of the present invention. The first observation optical system 11 and the illumination optical system 15 are disposed within a housing i.e. a barrel 30. The variable power zoom optical systems 11a and 11b (11b is not shown) of the first observation optical system and the variable power zoom optical system 16 of the illumination optical system 15 are driven by a cam cylinder 31. The upper inside surface of the cam cylinder 31 is provided with gear teeth 35 mating with a driving gear 34 which is driven by an electric motor 32 through a reduction means 33.

Formed on a bottom plate 36 of the barrel 30 are two left and right openings 37a and 37b (37b is not shown) for the first observation optical system 11. The projecting lens 17 of the illumination optical system 15 is fitted within an opening 38 formed on the bottom plate 36.

The reflecting prism 18 is mounted on a seat base 41 formed on one end of a swing arm 40. The swing arm 40 is swingably mounted on a stepped pin 43 fixed on the bottom plate 36 of the barrel 30. A pin 44 is fixed on the other end of the swing arm 40, as shown in FIG. 3. The pin 44 engages with a fork shaped piece 51 inserted into a ring 50 which is mounted on the barrel 30 rotatably around the optical axis $O_1$ of the objective lens 10. Formed on the external end of the fork shaped piece 51 is a thread 52 on which a sterilizeable knob 53 is detachably mounted. Only to this structure, it is possible to put the reflecting prism 18 within the illumination ray path and retract the prism 18 therefrom by rotating the knob 53 in the direction of an arrow 54 and therefore rotating the swing arm 40 around the pin 43.

Another ring 60 is further mounted on the barrel 30 at the lower end thereof rotatably around the optical axis $O_1$ of the objective ens 10 as shown in FIG. 2. As clearly shown in FIGS. 2 and 4, mounted on the ring 60 are two diametrically opposed supporting arms 62a and 62b respectively having seat bases 64a and 64b on which openings 63a and 63b are respectively formed. The seat bases 64a and 64b respectively support the reflecting prisms 13a and 13b thereon. An opening 66 is formed on the side wall of the ring 60 and forms a passage for the exit optical axes $O'_{3a}$ and $O'_{3b}$ from the reflecting prisms 13a and 13b. A mount 67 having a dovetail flange 65 projects from the opening 66 and supports the microscope for assistance, which has a dovetail flange 90, through dovetail connection. The objective lens 10 is threadably mounted on the lower end of the ring 60 through a screw mount 61.

By rotating the ring 60 by a small angle in the direction of the arrow 70, the microscope for assistant can be rotated around the optical axis $O_1$ within a range in which the reflecting prisms 13a and 13b on the seat bases 64a and 64b do not block off the optical axes of the first observation system 11. On the other hand, the exit optical axes $O'_{3a}$ and $O'_{3b}$ of the reflecting prisms 13a and 13b can be turned to the position shown by dotted lines in FIG. 4 by rotating the ring 60 by 180°. Accordingly, it is possible to selectively position the microscope for assistant either at the lefthand side or at the righthand side of the operator.

Figure 5:
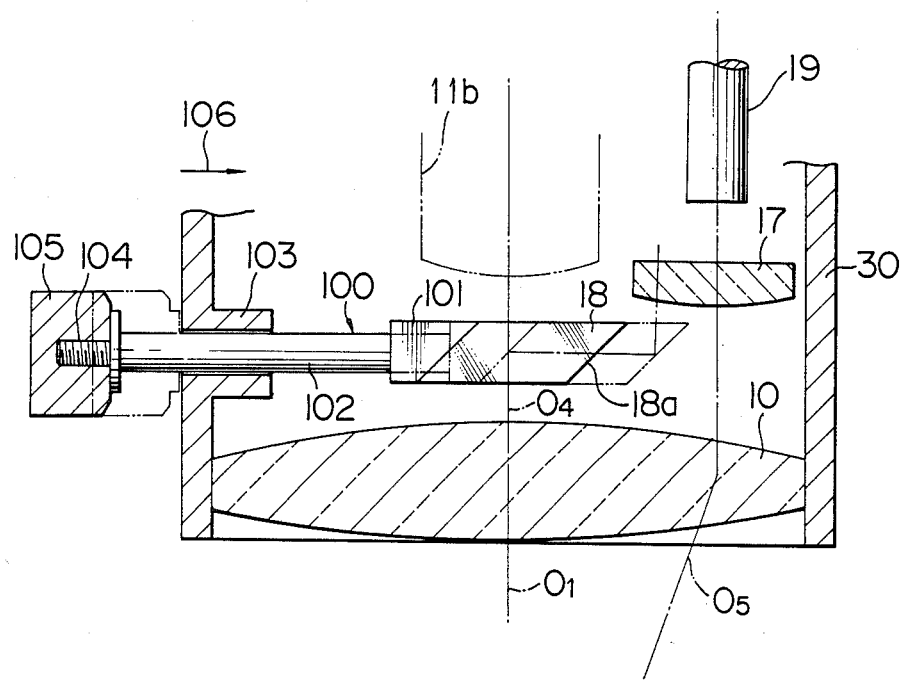
FIG. 5 is a longitudinal cross-sectional view showing a second embodiment of the present invention.

FIG. 5 shows a second embodiment of the present invention wherein the reflecting prism 18 is mounted on a seat base 101 of a slider 100. The slider 100 has a shank 102 which is slidably inserted into a bearing 103 of the barrel 30 in a direction perpendicular to the optical axis $O_1$ of the objective lens 10. The shank 102 is provided with a thread 104 on the external end thereof on which a sterilizeable knob 105 is threadably mounted. By pushing the knob 105 in the direction of the arrow 106, the reflecting prism 18 is horizontally moved and the reflecting surface 18a thereof is shifted to a position beneath the projecting lens 17 as shown by a phantom line. In this condition, one part of the illumination rays are projected through the optical axis $O_1$ of the objective lens 10.

Figure 6:
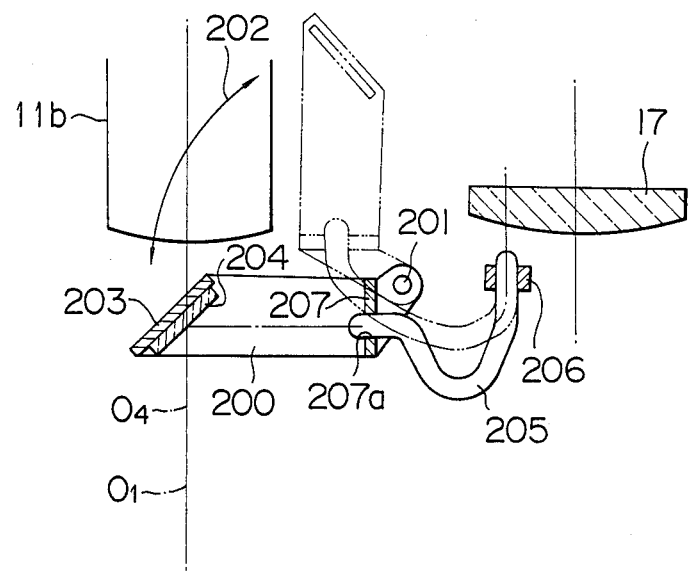
FIG. 6 is a longitudinal cross-sectional view showing a third embodiment of the present invention.

FIG. 6 shows a third embodiment of the present invention wherein a swing arm 200 is mounted on a pin 201 fixed on the barrel 30 swingably around the pin 201 along an arrow 202. A reflecting mirror 204 is mounted on a flange 203 formed on one end of the swing arm 200. Formed on the other end of the swing arm 200 is a flange 207 having an opening 207a through which one end of an optical fiber having rounded ends is passed. The other end of the optical fiber 205 is supported by a bracket 206 beneath the projecting lens 17. By turning the swing arm 200 from a retracted position as shown by a phantom line in FIG. 6 to a position shown by a solid line, it is possible to direct the illumination rays from the projecting lens 17 to the objective lens 10 (not shown in FIG. 6) along its optical axis $O_1$.

As explained above, it is possible according to the present invention to project the illumination rays along the optical axis of the objective lens and therefore to sufficiently illuminate deep parts to be operated on.

The invention has thus been shown and described with reference to specific embodiments. However, it should be noted that the invention is in no way limited to the details of the illustrated arrangements but changes and modifications may be made without departing from the scope of the appended claims.

What is claimed is:

1. An operation microscope comprising:
a single objective lens having an optical axis;
a pair of observation optical systems behind said single objective lens;
illumination means disposed behind said single objective lens for projecting illumination light flux through a part of the peripheral portion of said single objective lens; and
transmission means having an exit optical axis and disposed between said objective lens and said illumination means, said transmission means being selectively positionable in and out of said optical axis of said single objective lens and said exit optical axis of said transmission means being substantially coincident with said optical axis of said single objective lens when said transmission means is moved in line with said optical axis of said single objective lens, so that a part of the illumination light flux ejected from said illumination means is transmitted through said transmission means and projected along said optical axis of said single objective lens.

2. An operation microscope according to claim 1, wherein said transmission means includes a reflecting member having at least two reflection surfaces, one of which has said exit optical axis.

3. An operation microscope according to claim 2, wherein said reflecting member is swingably mounted around in axis which is parallel with said optical axis of said single objective lens.

4. An operation microscope according to claim 2, wherein said reflecting member is slideably mounted in a direction which is perpendicular to said optical axis of said single objective lens.

5. An operation microscope according to claim 1, wherein said transmission means includes an arm member, a reflection surface and an optical fiber;
- said reflection surface being mounted on said arm member and having said exit optical axis;
- said optical fiber having an exit end which is mounted on said arm member; and
- said arm member being swingably mounted around an axis which is perpendicular to said optical axis of said single objective lens.

* * * * *